(12) United States Patent
Kane et al.

(10) Patent No.: US 10,589,101 B2
(45) Date of Patent: Mar. 17, 2020

(54) SYSTEM AND METHOD FOR DETECTING TAMPONADE

(71) Applicant: Cardiac Pacemakers, Inc., St. Paul, MN (US)

(72) Inventors: Michael J. Kane, Roseville, MN (US); Allan Charles Shuros, St. Paul, MN (US); Brian L. Schmidt, White Bear Lake, MN (US); Keith R. Maile, New Brighton, MN (US); Benjamin J. Haasl, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 16/192,420

(22) Filed: Nov. 15, 2018

(65) Prior Publication Data

US 2019/0083791 A1    Mar. 21, 2019

Related U.S. Application Data

(63) Continuation of application No. 15/244,571, filed on Aug. 23, 2016, now Pat. No. 10,159,842.
(Continued)

(51) Int. Cl.
*A61N 1/37*    (2006.01)
*A61B 5/02*    (2006.01)
(Continued)

(52) U.S. Cl.
CPC .......... *A61N 1/3704* (2013.01); *A61B 5/0031* (2013.01); *A61B 5/024* (2013.01);
(Continued)

(58) Field of Classification Search
None
See application file for complete search history.

(56) References Cited

U.S. PATENT DOCUMENTS 3,835,864 A    9/1974 Rasor et al.
3,943,936 A    3/1976 Rasor et al.
(Continued)

FOREIGN PATENT DOCUMENTS

AU    2008279789 B2    10/2011
AU    2008329620 B2    5/2014
(Continued)

OTHER PUBLICATIONS

US 8,886,318 B2, 11/2014, Jacobson et al. (withdrawn)
(Continued)

*Primary Examiner* — Erica S Lee
(74) *Attorney, Agent, or Firm* — Seager, Tufte & Wickhem LLP.

(57) ABSTRACT

Systems, methods, and devices for determining occurrences of a tamponade condition are disclosed. One exemplary method includes monitoring an accelerometer signal of a leadless cardiac pacemaker attached to a heart wall, determining if a tamponade condition of the patient's heart is indicated based at least in part on the monitored accelerometer signal, and in response to determining that the tamponade condition is indicated, providing a notification of the tamponade condition for use by a physician to take corrective action.

19 Claims, 9 Drawing Sheets

Related U.S. Application Data

(60) Provisional application No. 62/211,333, filed on Aug. 28, 2015.

(51) Int. Cl.
*A61B 5/024* (2006.01)
*A61B 5/00* (2006.01)
*A61N 1/05* (2006.01)
*A61N 1/375* (2006.01)
*A61B 5/029* (2006.01)
*A61B 5/11* (2006.01)

(52) U.S. Cl.
CPC .......... *A61B 5/029* (2013.01); *A61B 5/02028* (2013.01); *A61B 5/11* (2013.01); *A61B 5/6869* (2013.01); *A61N 1/057* (2013.01); *A61N 1/3756* (2013.01); *A61B 2562/0219* (2013.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,480,412 A | 1/1996 | Mouchawar et al. |
| 5,496,361 A | 3/1996 | Moberg et al. |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,549,652 A | 8/1996 | McClure et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |

(56) References Cited

U.S. PATENT DOCUMENTS

| | | |
|---|---|---|
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,002,963 A | 12/1999 | Mouchawar |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Colson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,267 B1 | 10/2001 | Rosborough et al. |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |

(56) References Cited

U.S. PATENT DOCUMENTS

| | | |
|---|---|---|
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,267,649 B2 | 9/2007 | Zdeblick et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,890,185 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,963,925 B1 | 6/2011 | Schecter |
| 7,974,702 B1 | 7/2011 | Fain et al. |
| 7,979,136 B2 | 7/2011 | Young et al. |
| 7,983,753 B2 | 7/2011 | Severin |

(56) References Cited

U.S. PATENT DOCUMENTS

| | | |
|---|---|---|
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,128,569 B1 | 3/2012 | Mason et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bomzin et al. |
| 8,788,035 B2 | 7/2014 | Jacobson |
| 8,788,053 B2 | 7/2014 | Jacobson |

(56) References Cited

U.S. PATENT DOCUMENTS

| | | |
|---|---|---|
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bomzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bomzin et al. |
| 9,433,368 B2 | 9/2016 | Stahmann et al. |
| 9,433,780 B2 | 9/2016 | Régnier et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0163054 A1 | 8/2003 | Dekker |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260346 A1 | 12/2004 | Overall et al. |
| 2004/0260348 A1 | 12/2004 | Bakken et al. |
| 2004/0267303 A1 | 12/2004 | Guenst |
| 2005/0061320 A1 | 3/2005 | Lee et al. |

(56) References Cited

U.S. PATENT DOCUMENTS

| | | |
|---|---|---|
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0161211 A1 | 7/2006 | Thompson et al. |
| 2006/0178586 A1 | 8/2006 | Dobak |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0032749 A1* | 2/2007 | Overall ............... A61B 5/02444 600/595 |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0281214 A1* | 11/2008 | Elle ......................... A61B 5/029 600/508 |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2008/0306539 A1 | 12/2008 | Zdeblick et al. |
| 2009/0018599 A1 | 1/2009 | Hastings et al. |
| 2009/0024180 A1 | 1/2009 | Kisker et al. |
| 2009/0036777 A1* | 2/2009 | Zhang ................. A61B 5/0031 600/459 |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0177069 A1 | 7/2009 | Razavi |
| 2009/0204163 A1 | 8/2009 | Shuros et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0106030 A1 | 4/2010 | Mason |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |

(56) References Cited

U.S. PATENT DOCUMENTS

| | | |
|---|---|---|
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172688 A1 | 7/2012 | Mason et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bomzin et al. |
| 2013/0110192 A1 | 5/2013 | Tran et al. |
| 2013/0110219 A1 | 5/2013 | Bomzin et al. |
| 2013/0116529 A1 | 5/2013 | Min et al. |
| 2013/0116738 A1 | 5/2013 | Samade et al. |
| 2013/0116740 A1 | 5/2013 | Bomzin et al. |
| 2013/0116741 A1 | 5/2013 | Bomzin et al. |
| 2013/0123872 A1 | 5/2013 | Bomzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0200481 A1* | 7/2014 | Johnson ............ A61M 5/14236 600/561 |
| 2014/0207149 A1 | 7/2014 | Hastings et al. |
| 2014/0207210 A1 | 7/2014 | Willis et al. |
| 2014/0214104 A1 | 7/2014 | Greenhurst et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0231710 A1 | 8/2014 | Nelson et al. |
| 2014/0236172 A1 | 8/2014 | Hastings et al. |
| 2014/0243848 A1 | 8/2014 | Auriccio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0296714 A1* | 10/2014 | Kuroki ............ A61B 8/04 600/450 |
| 2014/0303704 A1 | 10/2014 | Suwito et al. |

(56) References Cited

U.S. PATENT DOCUMENTS

| | | |
|---|---|---|
| 2014/0309706 A1 | 10/2014 | Jacobson |
| 2014/0379041 A1 | 12/2014 | Foster |
| 2015/0025612 A1 | 1/2015 | Haasl et al. |
| 2015/0032007 A1* | 1/2015 | Ottevanger ......... A61B 5/6869 600/465 |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1* | 1/2016 | Cho ................... A61N 1/36578 607/18 |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0331888 A1 | 11/2016 | Koolbergen et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| JP | 5199867 B2 | 5/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 020988282 A2 | 5/2003 |
| WO | 2004066825 A2 | 8/2004 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A2 | 11/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |

OTHER PUBLICATIONS

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration, Jan. 29, 2016, 15 pages.

Spickler et al., "Totally Self-Contained Intracardiac Pacemaker," Journal of Electrocardiology, vol. 3(3&4): 324-331, 1970.

"Instructions for Use System 1, Leadless Cardiac Pacemaker (LCP) and Delivery Catheter," Nanostim Leadless Pacemakers, pp. 1-28, 2013.

Notification of Transmittal of the International Search Report and the Written opinion of the International Searching Authority, or the Declaration dated Jan. 29, 2016, 15 pages.

International Search Report and Written Opinion for Application No. PCT/US2016/048180, 11 pages, dated Dec. 5, 2016.

* cited by examiner

SYSTEM AND METHOD FOR DETECTING TAMPONADE

CROSS REFERENCE TO RELATED APPLICATIONS

This is a continuation of co-pending U.S. patent application Ser. No. 15/244,571 filed on Aug. 23, 2016, which claims the benefit of U.S. Provisional Patent Application Ser. No. 62/211,333 filed on Aug. 28, 2015, both of which are incorporated herein by reference.

TECHNICAL FIELD

The present disclosure generally relates to systems, devices, and methods for detecting a tamponade condition, and more particularly, to systems, devices, and methods for detecting a tamponade condition using one or more signals sensed by an implanted medical device.

BACKGROUND

Pacing instruments can be used to treat patients suffering from various heart conditions that result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) may be implanted in a patient's body. Such devices may monitor and provide electrical stimulation to the heart to help the heart operate in a more normal, efficient and/or safe manner. In some cases, such devices may be attached, at least partially, to the heart.

SUMMARY

The present disclosure generally relates to systems, devices, and methods for detecting a tamponade condition, and more particularly, to systems, devices, and methods for detecting a tamponade condition using one or more signals sensed by an implanted medical device. In a first illustrative embodiment, a leadless cardiac pacemaker for use in pacing a patient's heart may comprise a plurality of electrodes, an accelerometer for providing an accelerometer signal. The leadless cardiac pacemaker may further comprise a controller operatively coupled to the plurality of electrodes and the accelerometer. The leadless cardiac pacemaker may be implanted into a patient's heart and attached to a wall of the patient's heart using one or more fixation elements. In some instances, fixing the fixation elements to the patient's heart may cause a tamponade condition. In some instances, the controller may be configured to monitor the accelerometer signal of the leadless cardiac pacemaker and determine if a tamponade condition of the patient's heart is indicated based at least in part on the monitored accelerometer signal. If the controller determines that a tamponade condition is indicated, the controller may provide a notification of the tamponade condition for use by a physician to take corrective action.

Additionally, or alternatively, in some embodiments according to the first illustrative embodiment, to determine if a tamponade condition of the patient's heart is indicated based at least in part on the monitored accelerometer signal, the controller may be configured to identify a characteristic of the accelerometer signal, determine if the identified characteristic changes (e.g. diminishes) over time, and determine that the tamponade condition is indicated if the identified characteristic of the of the accelerometer signal changes (e.g. diminishes) over time.

Additionally, or alternatively, in any of the above embodiments according to the first illustrative embodiment, the identified characteristic may comprise a peak amplitude of the accelerometer signal.

Additionally, or alternatively, in any of the above embodiments according to the first illustrative embodiment, the identified characteristic may comprise a peak amplitude of an integral of the accelerometer signal.

Additionally, or alternatively, in any of the above embodiments according to the first illustrative embodiment, determining if the identified characteristic diminishes over time may comprise determining if the identified characteristic falls below a predetermined threshold.

Additionally, or alternatively, in any of the above embodiments according to the first illustrative embodiment, wherein the accelerometer signal may represent one axis of a multi-axis accelerometer.

Additionally, or alternatively, in any of the above embodiments according to the first illustrative embodiment, the accelerometer signal may represent a summed signal of all axes of a multi-axis accelerometer.

Additionally, or alternatively, in any of the above embodiments according to the first illustrative embodiment, to provide the notification, the controller may be configured to communicate a message to an external device programmer.

Additionally, or alternatively, in any of the above embodiments according to the first illustrative embodiment, the notification of the tamponade condition may be communicated using two or more of the plurality of electrodes of the leadless cardiac pacemaker.

Additionally, or alternatively, in any of the above embodiments according to the first illustrative embodiment, to determine if a tamponade condition of the patient's heart is indicated based at least in part on the monitored accelerometer signal, the controller may be configured to determine if a feature of the accelerometer signal falls below a first threshold.

Additionally, or alternatively, in any of the above embodiments according to the first illustrative embodiment, to determine if a tamponade condition of the patient's heart is indicated based at least in part on the monitored accelerometer signal, the controller may be further configured to determine if the feature of the accelerometer signal rises above a second threshold within a predetermined period of time, and determine that the tamponade condition is indicated if the feature of the accelerometer signal does not rise above the second threshold within the predetermined period of time.

Additionally, or alternatively, in any of the above embodiments according to the first illustrative embodiment, to determine if a tamponade condition of the patient's heart is indicated based at least in part on the monitored accelerometer signal, the controller may be further configured to determine whether the feature of the accelerometer signal has diminished below a second threshold value before rising above a third threshold value, and determine that the tamponade condition is indicated if the feature of the accelerometer signal has diminished below the second threshold value before rising above the third threshold value.

Additionally, or alternatively, in any of the above embodiments according to the first illustrative embodiment, the third threshold value may be less than the first threshold value.

Additionally, or alternatively, in any of the above embodiments according to the first illustrative embodiment, the leadless cardiac pacemaker may further comprise a pressure sensor, and the controller the controller may be further configured to monitor a cardiac electrical signal sensed via the plurality of electrodes, determine if a tamponade condition of the patient's heart is indicated based at least in part on the sensed cardiac electrical signal, and in response to determining that the tamponade condition is indicated, provide a notification of the tamponade condition for use by a physician to take corrective action.

Additionally, or alternatively, in any of the above embodiments according to the first illustrative embodiment, to determine if a tamponade condition of the patient's heart is indicated based at least in part on the intracardiac signal, the controller may be configured to determine if a detected peak amplitude of the intracardiac pressure signal diminishes below a threshold value.

In a second illustrative embodiment, a method for detecting a tamponade condition of a patient's heart after attachment of a leadless cardiac pacemaker to the patient's heart, the leadless cardiac pacemaker having an accelerometer that produces an accelerometer signal, may comprise monitoring the accelerometer signal of the leadless cardiac pacemaker, determining if a tamponade condition of the patient's heart is indicated based at least in part on the monitored accelerometer signal, and in response to determining that the tamponade condition is indicated, providing a notification of the tamponade condition for use by a physician to take corrective action.

Additionally, or alternatively, in any of the above embodiments according to the second illustrative embodiment, the determining step may comprise identifying a characteristic of the accelerometer signal, determining if the identified characteristic diminishes over time, and determining that the tamponade condition is indicated if the identified characteristic of the of the accelerometer signal diminishes over time.

Additionally, or alternatively, in any of the above embodiments according to the second illustrative embodiment, the identified characteristic may comprise a peak amplitude of the accelerometer signal.

Additionally, or alternatively, in any of the above embodiments according to the second illustrative embodiment, the identified characteristic may comprise a peak amplitude of an integral of the accelerometer signal.

Additionally, or alternatively, in any of the above embodiments according to the second illustrative embodiment, the accelerometer signal may represent one axis of a multi-axis accelerometer.

Additionally, or alternatively, in any of the above embodiments according to the second illustrative embodiment, the accelerometer signal may represent a summed signal of all axes of a multi-axis accelerometer.

Additionally, or alternatively, in any of the above embodiments according to the second illustrative embodiment, determining if the identified characteristic diminishes over time may comprise determining if the identified characteristic falls below a predetermined threshold.

Additionally, or alternatively, in any of the above embodiments according to the second illustrative embodiment, the leadless cardiac pacemaker may perform the monitoring, determining and providing steps.

Additionally, or alternatively, in any of the above embodiments according to the second illustrative embodiment, the leadless cardiac pacemaker may perform the monitoring step.

Additionally, or alternatively, in any of the above embodiments according to the second illustrative embodiment, an external device programmer may perform one or more of the monitoring, determining and providing steps.

Additionally, or alternatively, in any of the above embodiments according to the second illustrative embodiment, providing the notification may comprise communicating a message from the leadless cardiac pacemaker for reception by an external device programmer.

In a third illustrative embodiment, a leadless cardiac pacemaker for use in pacing a patient's heart may comprise a plurality of electrodes, an accelerometer for providing an accelerometer signal, and a controller operatively coupled to the plurality of electrodes and the accelerometer. In at least some embodiments, the controller may be configured to monitor the accelerometer signal of the accelerometer over time, determine if a tamponade condition of the patient's heart is indicated based at least in part on the monitored accelerometer signal, and, in response to determining that the tamponade condition is indicated, communicate a notification of the tamponade condition for use by a physician to take corrective action.

Additionally, or alternatively, in any of the above embodiments according to the third illustrative embodiment, the notification of the tamponade condition may be communicated using two or more of the plurality of electrodes of the leadless cardiac pacemaker.

Additionally, or alternatively, in any of the above embodiments according to the third illustrative embodiment, to determine if the tamponade condition of the patient's heart is indicated, the controller may be configured to identify a characteristic of the accelerometer signal, determine if the identified characteristic diminishes over time, and determine that the tamponade condition is indicated if the identified characteristic of the of the accelerometer signal diminishes over time.

Additionally, or alternatively, in any of the above embodiments according to the third illustrative embodiment, the identified characteristic may comprise a peak amplitude of the accelerometer signal.

Additionally, or alternatively, in any of the above embodiments according to the third illustrative embodiment, the identified characteristic may comprise a peak amplitude of an integral of the accelerometer signal.

In a fourth illustrative embodiment, a leadless cardiac pacemaker may comprise a plurality of electrodes, an accelerometer for providing an accelerometer signal, a controller operatively coupled to the plurality of electrodes and the accelerometer. In at least some embodiments, the controller may be configured to monitor an indication of a range of physical motion of a patient's heart over time using the accelerometer signal, determine if the indication of the range of physical motion of the patient's heart reduces over time by at least a predefined amount, and, if it is determined that the indication of the range of physical motion of the patient's heart has reduced over time by at least the predefined amount, communicate a notification of a possible tamponade condition for reception by a remote device that is remote from the leadless cardiac pacemaker.

Additionally, or alternatively, in any of the above embodiments according to the fourth illustrative embodiment, the controller may be further configured to monitor a heart rate of the patient's heart over time and to determine if the heart rate increases over time by at least a predetermined heart rate amount.

Additionally, or alternatively, in any of the above embodiments according to the fourth illustrative embodiment, the controller may only communicate a notification of the possible tamponade condition if it is determined that the indication of the range of physical motion of the patient's heart has reduced over time by at least the predefined amount and the heart rate of the patient's heart has increased over time by at least the predetermined heart rate amount.

Additionally, or alternatively, in any of the above embodiments according to the fourth illustrative embodiment, the notification of the possible tamponade condition may be communicated using two or more of the plurality of electrodes of the leadless cardiac pacemaker.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
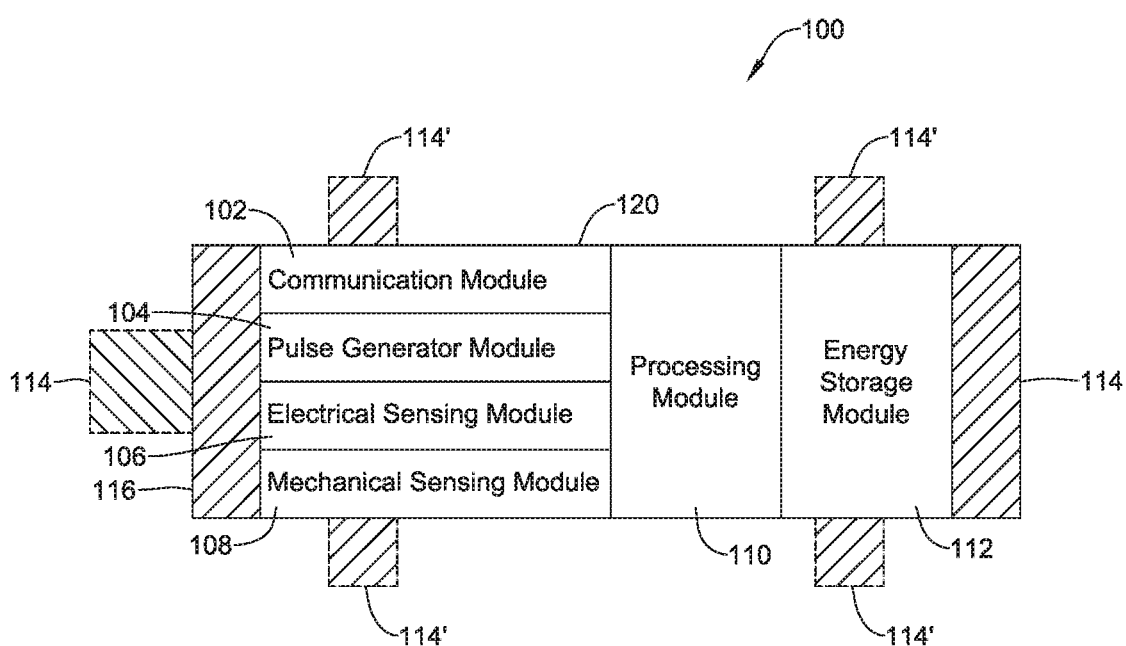
FIG. 1 is a schematic block diagram of an illustrative leadless cardiac pacemaker (LCP) according to one embodiment of the present disclosure.

While the disclosure is amenable to various modifications and alternative forms, specifics thereof have been shown by way of embodiment in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

This disclosure describes systems, devices, and methods for detecting a tamponade condition. Cardiac tamponade is a medical condition characterized by compression of the heart due to an accumulation of fluid in the pericardial sac. When a patient is experiencing cardiac tamponade, the electrical system of the heart may be functioning normally. The heart may still be generating intrinsic electrical signals in a normal rhythm, and the generated signals may propagate throughout the heart in a normal fashion. However, since the heart is being compressed by fluid in the pericardial sac, the heart muscle may not be able to relax from a contracted state, thereby limiting the ability of the heart to sufficiently pump blood.

Specifically in relation to medical devices, tamponade may be caused by attaching a medical device or leads of the medical device to the heart. Generally, a medical device or lead may have a fixation element to securely place the device or lead at a location on or within the heart. During implantation, the fixation element may end up puncturing through the heart wall or an artery or other vessel on the outside of the heart, resulting in a leak of blood between the heart muscle and the pericardial sac. As the leak continues, more blood may seep between the heart muscle and the pericardial sac, resulting in continually decreasing pumping action, potentially resulting in a dangerous situation for the patient. The present disclosure describes devices, systems, and techniques for monitoring one or more signals to determine whether a tamponade condition is occurring.

FIG. 1 is a conceptual schematic block diagram of an exemplary leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 1, LCP 100 may be a compact device with all components housed within LCP 100 or directly on housing 120. In some instances, LCP 100 may include communication module 102, pulse generator module 104, electrical sensing module 106, mechanical sensing module 108, processing module 110, energy storage module 112, and electrodes 114.

As depicted in FIG. 1, LCP 100 may include electrodes 114, which can be secured relative to housing 120 and electrically exposed to tissue and/or blood surrounding LCP 100. Electrodes 114 may generally conduct electrical signals to and from LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG).

Electrodes 114 may include one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 are secured directly to housing 120, an insulative material may electrically isolate the electrodes 114 from adjacent electrodes, housing 120, and/or other parts of LCP 100. In some instances, some or all of electrodes 114 may be spaced from housing 120 and connected to housing 120 and/or other components of LCP 100 through connecting wires. In such instances, the electrodes 114 may be placed on a tail (not shown) that extends out away from the housing 120. As shown in FIG. 1, in some embodiments, LCP 100 may include electrodes 114'. Electrodes 114' may be in addition to electrodes 114, or may replace one or more of electrodes 114. Electrodes 114' may be similar to electrodes 114 except that electrodes 114' are disposed on the sides of LCP 100. In some cases, electrodes 114' may increase the number of electrodes by which LCP 100 may deliver communication signals and/or electrical stimulation pulses, and/or may sense intrinsic cardiac electrical signals, communication signals, and/or electrical stimulation pulses.

Electrodes 114 and/or 114' may assume any of a variety of sizes and/or shapes, and may be spaced at any of a variety of spacings. For example, electrodes 114 may have an outer diameter of two to twenty millimeters (mm). In other embodiments, electrodes 114 and/or 114' may have a diameter of two, three, five, seven millimeters (mm), or any other suitable diameter, dimension and/or shape. Example lengths for electrodes 114 and/or 114' may include, for example, one, three, five, ten millimeters (mm), or any other suitable length. As used herein, the length is a dimension of electrodes 114 and/or 114' that extends away from the outer surface of the housing 120. In some instances, at least some of electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the embodiment shown, communication module 102 may be electrically coupled to electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. Communication module 102 may additionally be configured to sense for communication signals delivered by other devices, which may be located external or internal to the patient's body.

Communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 100 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 102 (or LCP 100) may further include switching circuitry to selectively connect one or more of electrodes 114 and/or 114' to communication module 102 in order to select which electrodes 114 and/or 114' that communication module 102 delivers communication pulses. It is contemplated that communication module 102 may be communicating with other devices via conducted signals, radio frequency (RF) signals, optical signals, acoustic signals, inductive coupling, and/or any other suitable communication methodology. Where communication module 102 generates electrical communication signals, communication module 102 may include one or more capacitor elements and/or other charge storage devices to aid in generating and delivering communication signals. In the embodiment shown, communication module 102 may use energy stored in energy storage module 112 to generate the communication signals. In at least some examples, communication module 102 may include a switching circuit that is connected to energy storage module 112 and, with the switching circuitry, may connect energy storage module 112 to one or more of electrodes 114/114' to generate the communication signals.

As shown in FIG. 1, a pulse generator module 104 may be electrically connected to one or more of electrodes 114 and/or 114'. Pulse generator module 104 may be configured to generate electrical stimulation pulses and deliver the electrical stimulation pulses to tissues of a patient via one or more of the electrodes 114 and/or 114' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In some of these cases, LCP 100 may vary the rate at which pulse generator 104 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. When used to treat other ailments, the pulse generator module 104 may generate electrical stimulation pulses suitable for neurostimulation therapy or the like. Pulse generator module 104 may include one or more capacitor elements and/or other charge storage devices to aid in generating and delivering appropriate electrical stimulation pulses. In at least some embodiments, pulse generator module 104 may use energy stored in energy storage module 112 to generate the electrical stimulation pulses. In some particular embodiments, pulse generator module 104 may include a switching circuit that is connected to energy storage module 112 and may connect energy storage module 112 to one or more of electrodes 114/114' to generate electrical stimulation pulses.

LCP 100 may further include an electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114' via a sensor amplifier or the like. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, including multi-axis accelerometers such as two- or three-axis accelerometers, gyroscopes, including multi-axis gyroscopes such as two- or three-axis gyroscopes, blood pressure sensors, heart sound sensors, piezoelectric sensors, blood-oxygen sensors, and/or other sensors which measure one or more physiological parameters of the heart and/or patient. Mechanical sensing module 108, when present, may gather signals from the sensors indicative of the various physiological parameters. Both electrical sensing module 106 and mechanical sensing module 108 may be connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module. In at least some examples, LCP 100 may only include one of electrical sensing module 106 and mechanical sensing module 108. In some cases, any combination of the processing module 110, electrical sensing module 106, mechanical sensing module 108, communication module 102, pulse generator module 104 and/or energy storage module may be considered a controller of the LCP 100.

Processing module 110 may be configured to direct the operation of LCP 100 and may, in some embodiments, be termed a controller. For example, processing module 110 may be configured to receive cardiac electrical signals from electrical sensing module 106 and/or physiological signals from mechanical sensing module 108. Based on the received signals, processing module 110 may determine, for example, occurrences and types of arrhythmias and other determinations such as whether LCP 100 has become dislodged. Processing module 110 may further receive information from communication module 102. In some embodiments, processing module 110 may additionally use such received information to determine occurrences and types of arrhythmias and/or and other determinations such as whether LCP 100 has become dislodged. In still some additional embodiments, LCP 100 may use the received information instead of the signals received from electrical sensing module 106 and/or mechanical sensing module 108—for instance if the received information is deemed to be more accurate than the signals received from electrical sensing module 106 and/or mechanical sensing module 108 or if electrical sensing module 106 and/or mechanical sensing module 108 have been disabled or omitted from LCP 100.

After determining an occurrence of an arrhythmia, processing module 110 may control pulse generator module 104 to generate electrical stimulation pulses in accordance with one or more electrical stimulation therapies to treat the determined arrhythmia. For example, processing module 110 may control pulse generator module 104 to generate pacing pulses with varying parameters and in different sequences to effectuate one or more electrical stimulation therapies. As one example, in controlling pulse generator module 104 to deliver bradycardia pacing therapy, processing module 110 may control pulse generator module 104 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, processing module 110 may monitor one or more physiological parameters of the patient which may indicate a need for an increased heart rate (e.g. due to increased metabolic demand). Processing module 110 may then increase the rate at which pulse generator 104 generates electrical stimulation pulses.

For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, processing module 110 may control pulse generator module 104 to reduce the rate of delivered pacing pulses down to a safer level. In CRT, processing module 110 may control pulse generator module 104 to deliver pacing pulses in coordination with another device to cause the heart to contract more efficiently. In cases where pulse generator module 104 is capable of generating defibrillation and/or cardioversion pulses for defibrillation/cardioversion therapy, processing module 110 may control pulse generator module 104 to generate such defibrillation and/or cardioversion pulses. In some cases, processing module 110 may control pulse generator module 104 to generate electrical stimulation pulses to provide electrical stimulation therapies different than those examples described above.

Aside from controlling pulse generator module 104 to generate different types of electrical stimulation pulses and in different sequences, in some embodiments, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may help LCP 100 provide more effective delivery of electrical stimulation therapy.

In some embodiments, processing module 110 may further control communication module 102 to send information to other devices. For example, processing module 110 may control communication module 102 to generate one or more communication signals for communicating with other devices of a system of devices. For instance, processing module 110 may control communication module 102 to generate communication signals in particular pulse sequences, where the specific sequences convey different information. Communication module 102 may also receive communication signals for potential action by processing module 110.

In further embodiments, processing module 110 may control switching circuitry by which communication module 102 and pulse generator module 104 deliver communication signals and/or electrical stimulation pulses to tissue of the patient. As described above, both communication module 102 and pulse generator module 104 may include circuitry for connecting one or more electrodes 114 and/114' to communication module 102 and/or pulse generator module 104 so those modules may deliver the communication signals and electrical stimulation pulses to tissue of the patient. The specific combination of one or more electrodes by which communication module 102 and/or pulse generator module 104 deliver communication signals and electrical stimulation pulses may influence the reception of communication signals and/or the effectiveness of electrical stimulation pulses. Although it was described that each of communication module 102 and pulse generator module 104 may include switching circuitry, in some embodiments, LCP 100 may have a single switching module connected to the communication module 102, the pulse generator module 104, and electrodes 114 and/or 114'. In such embodiments, processing module 110 may control the switching module to connect modules 102/104 and electrodes 114/114' as appropriate.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other instances, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip. In still other embodiments, processing module 110 may not be a single component. For example, processing module 110 may include multiple components positioned at disparate locations within LCP 100 in order to perform the various described functions. For example, certain functions may be performed in one component of processing module 110, while other functions are performed in a separate component of processing module 110.

Processing module 110, in additional embodiments, may include a memory circuit and processing module 110 may store information on and read information from the memory circuit. In other embodiments, LCP 100 may include a separate memory circuit (not shown) that is in communication with processing module 110, such that processing module 110 may read and write information to and from the separate memory circuit. The memory circuit, whether part of processing module 110 or separate from processing module 110, may be volatile memory, non-volatile memory, or a combination of volatile memory and non-volatile memory.

Energy storage module 112 may provide a power source to LCP 100 for its operations. In some embodiments, energy storage module 112 may be a non-rechargeable lithium-based battery. In other embodiments, the non-rechargeable battery may be made from other suitable materials. In some embodiments, energy storage module 112 may include a rechargeable battery. In still other embodiments, energy storage module 112 may include other types of energy storage devices such as capacitors or super capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. The one or more anchors 116 are shown schematically in FIG. 1. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, anchor 116 may include other structures such as barbs, spikes, or the like to facilitate engagement with the surrounding cardiac tissue.

In some examples, LCP 100 may be configured to be implanted on a patient's heart or within a chamber of the patient's heart. For instance, LCP 100 may be implanted within any of a left atrium, right atrium, left ventricle, or right ventricle of a patient's heart. By being implanted within a specific chamber, LCP 100 may be able to sense cardiac electrical signals originating or emanating from the specific chamber that other devices may not be able to sense with such resolution. Where LCP 100 is configured to be implanted on a patient's heart, LCP 100 may be configured to be implanted on or adjacent to one of the chambers of the heart, or on or adjacent to a path along which intrinsically generated cardiac electrical signals generally follow. In these examples, LCP 100 may also have an enhanced ability to sense localized intrinsic cardiac electrical signals and deliver localized electrical stimulation therapy.

Figure 2:
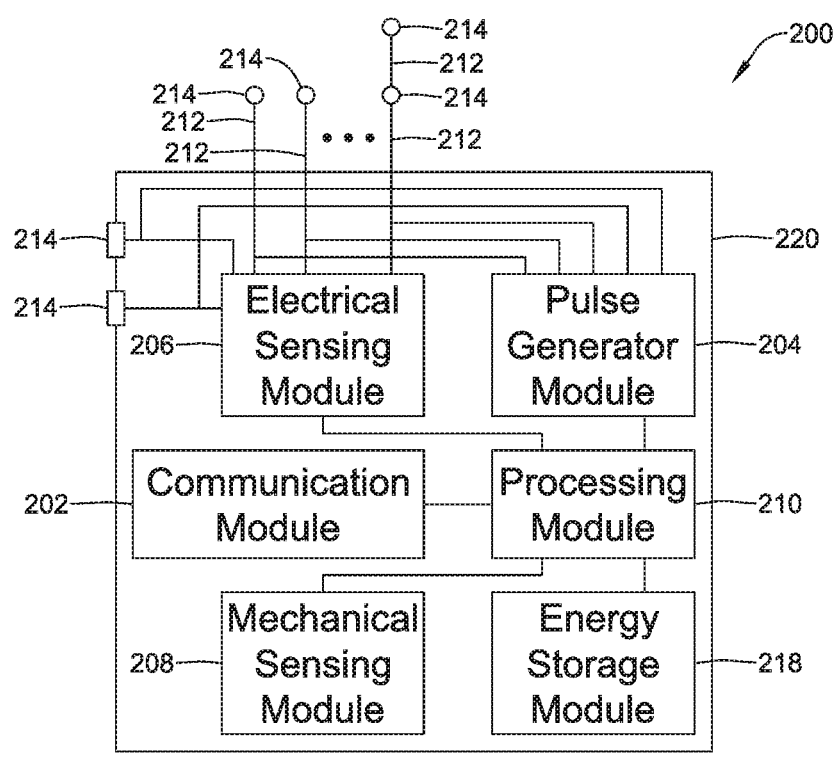
FIG. 2 is a schematic block diagram of another illustrative medical device that may be used in conjunction with the LCP of FIG. 1.

FIG. 2 depicts an embodiment of another device, medical device (MD) 200, which may operate to sense physiological signals and parameters and deliver one or more types of electrical stimulation therapy to tissues of the patient. In the embodiment shown, MD 200 may include a communication module 202, a pulse generator module 204, an electrical sensing module 206, a mechanical sensing module 208, a processing module 210, and an energy storage module 218. Each of modules 202, 204, 206, 208, and 210 may be similar to modules 102, 104, 106, 108, and 110 of LCP 100. Additionally, energy storage module 218 may be similar to energy storage module 112 of LCP 100. However, in some embodiments, MD 200 may have a larger volume within housing 220. In such embodiments, MD 200 may include a larger energy storage module 218 and/or a larger processing module 210 capable of handling more complex operations than processing module 110 of LCP 100.

While MD 200 may be another leadless device such as shown in FIG. 1, in some instances MD 200 may include leads, such as leads 212. Leads 212 may include electrical wires that conduct electrical signals between electrodes 214 and one or more modules located within housing 220. In some cases, leads 212 may be connected to and extend away from housing 220 of MD 200. In some embodiments, leads 212 are implanted on, within, or adjacent to a heart of a patient. Leads 212 may contain one or more electrodes 214 positioned at various locations on leads 212 and various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In other cases, the one or more of the electrodes 214 may be positioned subcutaneously but adjacent the patient's heart. The electrodes 214 may conduct intrinsically generated electrical cardiac signals to leads 212. Leads 212 may, in turn, conduct the received electrical cardiac signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical stimulation signals to the cardiac tissue of the patient (either directly or indirectly). MD 200 may also include one or more electrodes 214 not disposed on a lead 212. For example, one or more electrodes 214 may be connected directly to housing 220.

Leads 212, in some embodiments, may additionally contain one or more sensors, such as accelerometers, blood pressure sensors, heart sound sensors, blood-oxygen sensors, and/or other sensors which are configured to measure one or more physiological parameters of the heart and/or patient. In such embodiments, mechanical sensing module 208 may be in electrical communication with leads 212 and may receive signals generated from such sensors.

While not required, in some embodiments MD 200 may be an implantable medical device. In such embodiments, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body. In such embodiments, leads 212 may be implanted at one or more various locations within the patient, such as within the heart of the patient, adjacent to the heart of the patient, adjacent to the spine of the patient, or any other desired location.

In some embodiments, MD 200 may be an implantable cardiac pacemaker (ICP). In these embodiments, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some embodiments, MD 200 may additionally be configured to provide defibrillation/cardioversion therapy.

In some instances, MD 200 may be an implantable cardioverter-defibrillator (ICD). In such embodiments, MD 200 may include one or more leads implanted within a patient's heart. MD 200 may also be configured to sense electrical cardiac signals, determine occurrences of tachyarrhythmias based on the sensed electrical cardiac signals, and deliver defibrillation and/or cardioversion therapy in response to determining an occurrence of a tachyarrhythmia (for example by delivering defibrillation and/or cardioversion pulses to the heart of the patient). In other embodiments, MD 200 may be a subcutaneous implantable cardioverter-defibrillator (SICD). In embodiments where MD 200 is an SICD, one of leads 212 may be a subcutaneously implanted lead. In at least some embodiments where MD 200 is an SICD, MD 200 may include only a single lead which is implanted subcutaneously but outside of the chest cavity, however this is not required.

In some embodiments, MD 200 may not be an implantable medical device. Rather, MD 200 may be a device external to the patient's body, and electrodes 214 may be skin-electrodes that are placed on a patient's body. In such embodiments, MD 200 may be able to sense surface electrical signals (e.g. electrical cardiac signals that are generated by the heart or electrical signals generated by a device implanted within a patient's body and conducted through the body to the skin). MD 200 may further be configured to deliver various types of electrical stimulation therapy, including, for example, defibrillation therapy via skin-electrodes 214.

Figure 3:
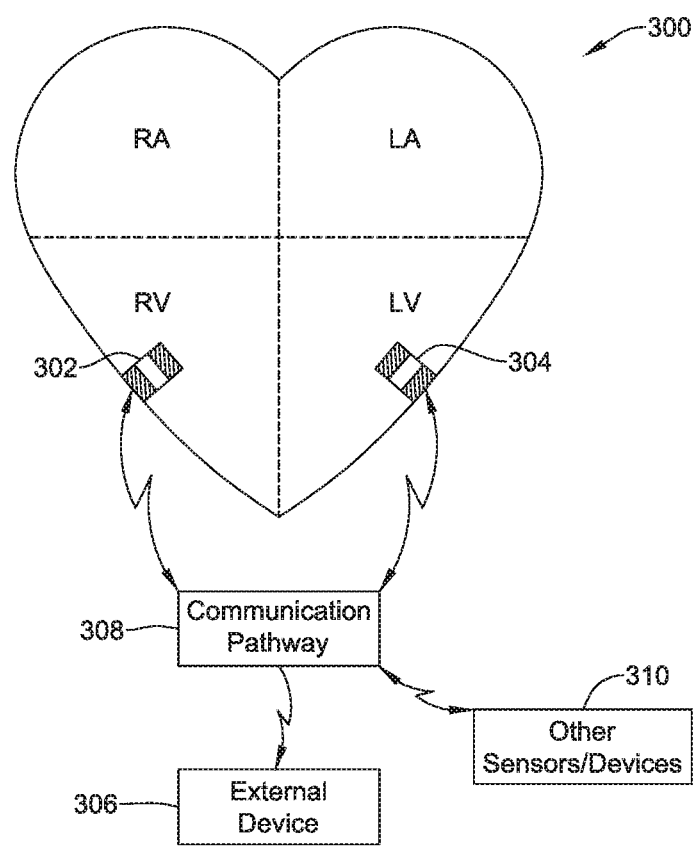
FIG. 3 is a schematic diagram of an exemplary medical system that includes multiple LCPs and/or other devices in communication with one another.

FIG. 3 illustrates an embodiment of a medical device system and a communication pathway through which multiple medical devices 302, 304, 306, and/or 310 of the medical device system may communicate. In the embodiment shown, medical device system 300 may include LCPs 302 and 304, external medical device 306, and other sensors/devices 310. External device 306 may be a device disposed external to a patient's body, as described previously with respect to MD 200. In at least some examples, external device 306 may represent an external support device such as a device programmer, as will be described in more detail below. Other sensors/devices 310 may be any of the devices described previously with respect to MD 200, such as ICPs, ICDs, and SICDs. Other sensors/devices 310 may also include various diagnostic sensors that gather information about the patient, such as accelerometers, blood pressure sensors, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one embodiment, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. One or more of devices 302/304, 306, and 310 of system 300 may additionally communicate command or response messages via communication pathway 308. The command messages may cause a receiving device to take a particular action whereas response messages may include requested information or a confirmation that a receiving device did, in fact, receive a communicated message or data.

It is contemplated that the various devices of system 300 may communicate via pathway 308 using RF signals, inductive coupling, optical signals, acoustic signals, or any other signals suitable for communication. Additionally, in at least some embodiments, the various devices of system 300 may communicate via pathway 308 using multiple signal types. For instance, other sensors/device 310 may communicate with external device 306 using a first signal type (e.g. RF communication) but communicate with LCPs 302/304 using a second signal type (e.g. conducted communication). Further, in some embodiments, communication between devices may be limited. For instance, as described above, in some embodiments, LCPs 302/304 may communicate with external device 306 only through other sensors/devices 310, where LCPs 302/304 send signals to other sensors/devices 310, and other sensors/devices 310 relay the received signals to external device 306.

In some cases, the various devices of system 300 may communicate via pathway 308 using conducted communication signals. Accordingly, devices of system 300 may have components that allow for such conducted communication. For instance, the devices of system 300 may be configured to transmit conducted communication signals (e.g. a voltage and/or current waveform punctuated with current and/or voltage pulses, referred herein as electrical communication pulses) into the patient's body via one or more electrodes of a transmitting device, and may receive the conducted communication signals via one or more electrodes of a receiving device. The patient's body may "conduct" the conducted communication signals from the one or more electrodes of the transmitting device to the electrodes of the receiving device in the system 300. In such embodiments, the delivered conducted communication signals may differ from pacing pulses, defibrillation and/or cardioversion pulses, or other electrical stimulation therapy signals. For example, the devices of system 300 may deliver electrical communication pulses at an amplitude/pulse width that is sub-threshold. That is, the communication pulses have an amplitude/pulse width designed to not capture the heart. In some cases, the amplitude/pulse width of the delivered electrical communication pulses may be above the capture threshold of the heart, but may be delivered during a refractory period of the heart and/or may be incorporated in or modulated onto a pacing pulse, if desired.

Additionally, unlike normal electrical stimulation therapy pulses, the electrical communication pulses may be delivered in specific sequences which convey information to receiving devices. For instance, delivered electrical communication pulses may be modulated in any suitable manner to encode communicated information. In some cases, the communication pulses may be pulse width modulated and/or amplitude modulated. Alternatively, or in addition, the time between pulses may be modulated to encode desired information. In some cases, a predefined sequence of communication pulses may represent a corresponding symbol (e.g. a logic "1" symbol, a logic "0" symbol, an ATP therapy trigger symbol, etc.). In some cases, conducted communication pulses may be voltage pulses, current pulses, biphasic voltage pulses, biphasic current pulses, or any other suitable electrical pulse as desired.

Figure 4:
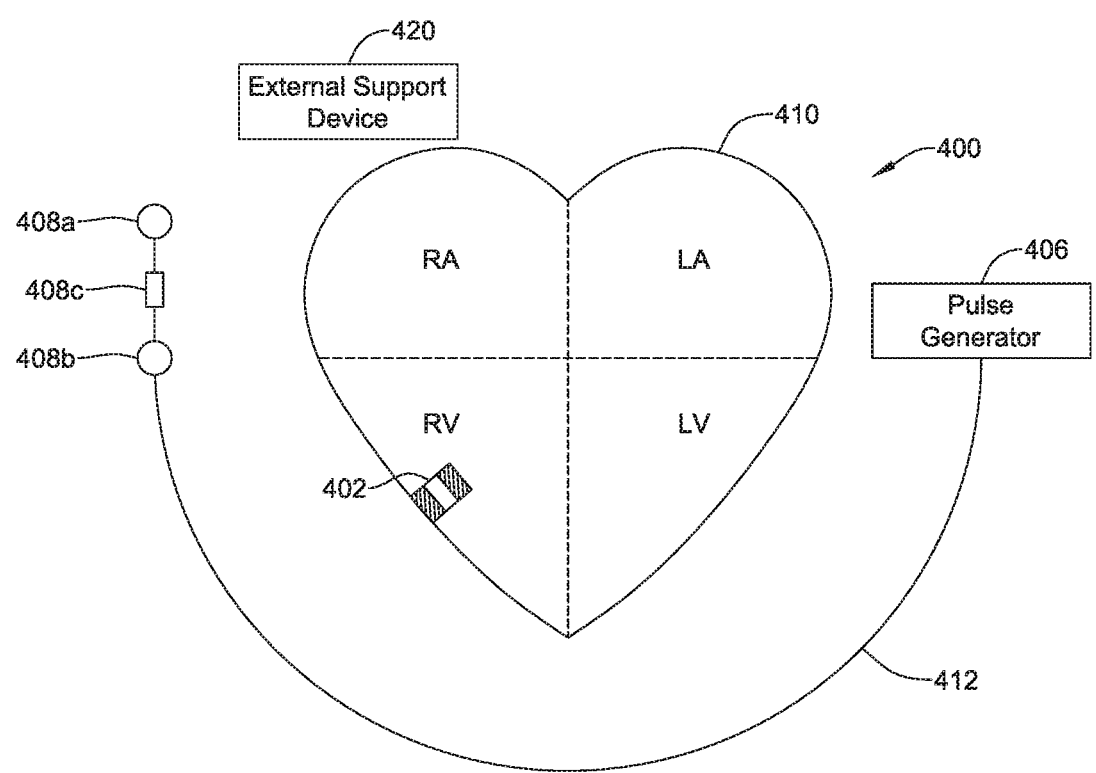
FIG. 4 is a schematic diagram of a system including an LCP and another medical device, in accordance with another embodiment of the present disclosure.

FIG. 4 depicts an illustrative medical device system 400 that may be configured to operate together. For example, system 400 may include multiple devices that are implanted within a patient and are configured to sense physiological signals, determine occurrences of cardiac arrhythmias, and deliver electrical stimulation to treat detected cardiac arrhythmias. In some embodiments, the devices of system 400 may be configured to determine occurrences of dislodgment of one or more devices of system 400. In FIG. 4, an LCP 402 is shown fixed to the interior of the right ventricle of the heart 410, and a pulse generator 406 is shown coupled to a lead 412 having one or more electrodes 408a-408c. In some cases, pulse generator 406 may be part of a subcutaneous implantable cardioverter-defibrillator (SICD), and the one or more electrodes 408a-408c may be positioned subcutaneously adjacent the heart. LCP 402 may communicate with the SICD, such as via communication pathway 308. The locations of LCP 402, pulse generator 406, lead 412, and electrodes 408a-c depicted in FIG. 4 are just exemplary. In other embodiments of system 400, LCP 402 may be positioned in the left ventricle, right atrium, or left atrium of the heart, as desired. In still other embodiments, LCP 402 may be implanted externally adjacent to heart 410 or even remote from heart 410.

Medical device system 400 may also include external support device 420. External support device 420 can be used to perform functions such as device identification, device programming and/or transfer of real-time and/or stored data between devices using one or more of the communication techniques described herein, or other functions involving communication with one or more devices of system 400. As one example, communication between external support device 420 and pulse generator 406 can be performed via a wireless mode, and communication between pulse generator 406 and LCP 402 can be performed via a conducted communication mode. In some embodiments, communication between LCP 402 and external support device 420 is accomplished by sending communication information through pulse generator 406. However, in other embodiments, communication between the LCP 402 and external support device 420 may be via a communication module.

FIG. 4 only illustrates one example embodiment of a medical device system that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs with or without other devices such as pulse generator 406, with at least one LCP capable of delivering defibrillation therapy. Still another example may include one or more LCPs implanted along with a transvenous pacemaker and with or without an implanted SICD. In yet other embodiments, the configuration or placement of the medical devices, leads, and/or electrodes may be different from those depicted in FIG. 4. Accordingly, it should be recognized that numerous other medical device systems, different from system 400 depicted in FIG. 4, may be operated in accordance with techniques disclosed herein. As such, the embodiment shown in FIG. 4 should not be viewed as limiting in any way.

In some embodiments, LCP 100 may be configured to determine whether a tamponade condition is occurring. For instance, LCP 100 may be configured to monitor one or more signals and determine, based on the one or more monitored signals, whether a tamponade condition is occurring within the heart. Additionally, or alternatively, LCP 100 may use one or more determined features or characteristics of the monitored signal or signals and determine whether tamponade is occurring based on the one or more determined features. In some embodiments, to determine whether a tamponade condition is occurring, LCP 100 may monitor a signal or a feature of the signal and determine whether the signal or the feature changes (e.g. diminishes) over time. Generally, diminishment of a signal or feature over time, such as diminishing below a threshold, may indicate that a tamponade condition is occurring. The below described techniques illustrate various signals and features that LCP 100 may monitor in order to determine whether a tamponade condition is occurring. In some cases, the LCP 100 may monitor one or more signals or features, and communicate information related to the one or more signals or features to a separate device. In some cases, the actual determination of whether a tamponade condition is occurring may be performed by the separate device.

In some embodiments, LCP 100 may be triggered to enter or exit a tamponade mode, where LCP 100 monitors for whether a tamponade condition is occurring. In some cases, the LCP may enter or exit the tamponade mode based on a communicated trigger signal. LCP 100 may receive such a trigger signal from a device external to LCP 100, such as support device 420, or may be internally generated. Generally, a user may trigger LCP 100, e.g. via external support device 420, to enter the tamponade mode at the time of implant and maintain LCP 100 in the tamponade mode throughout the implantation procedure and for a short time thereafter. A user may additionally trigger LCP 100 to enter the tamponade mode during follow-up procedures or appointments where the physician may be concerned that tamponade is a risk. Outside of these times, the physician may trigger tamponade detection off to save energy in the LCP.

Figure 5:
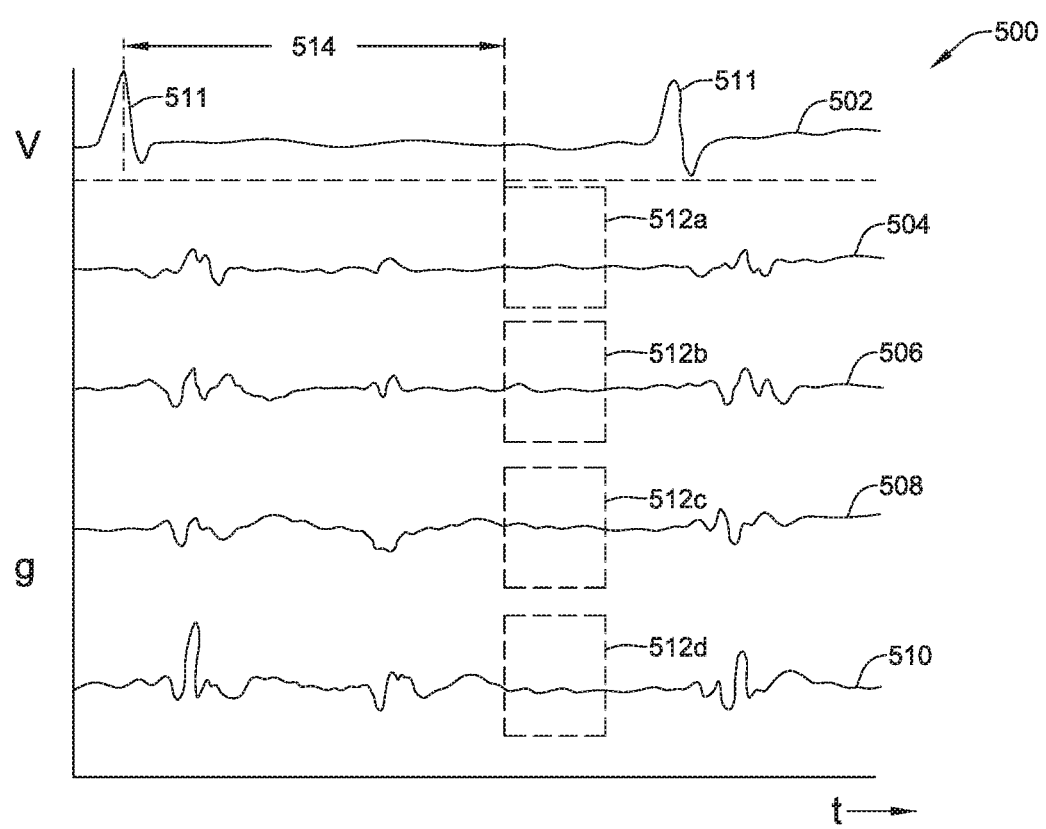
FIG. 5 is a graph showing an illustrative cardiac electrical signal and illustrative accelerometer signals detected by an LCP.

FIG. 5 is a graph 500 showing an illustrative cardiac electrical signal 502 (e.g. ECG) along with corresponding accelerometer signals 504, 506, 508 and 510 of a three axis accelerometer along a common time axis. The signal tracings of graph 500 may represent signals sensed or generated by an LCP 100 when LCP 100 is attached to a wall of a patients' heart. For example, signal 502 may represent a cardiac electrical signal 502 sensed by LCP 100. Signals 504, 506, and 508 may represent signals from different axes generated by a three-axis accelerometer of LCP 100. Signal 510 may represent an accelerometer magnitude signal, which may be determined by summing signals 504, 506, and 508 or summing the absolute values of signals 504, 506, and 508. In other embodiments, signal 510 may represent a different signal generated by other combinations of signals 504, 506, and 508, such as a root-mean-square or root-sum-square of signals 504, 506, and 508, or any other derivation of signals 504, 506, and 508.

LCP 100 may be configured to sense one or more of signals 504, 506, 508 and/or 510 during certain time periods. For instance, to "sense" one or more of the signals, it is contemplated that the LCP 100 may be configured to receive and process signals 504, 506, 508 and/or 510 at processing module 110. Whereas when the one or more of the signals are not being "sensed", processing module 110 of LCP 100 may not receive and/or process the signals 504, 506, 508 and/or 510. In some embodiments, to "sense" signals 504, 506, 508 and/or 510, LCP 100 may connect an output of the accelerometer to processing module 110 via a switch, multiplexer of the like. In other embodiments, the accelerometer may be configured to only output valid signals 504, 506, 508 and/or 510 when the accelerometer is to be sensed (e.g. the accelerometer may be enabled by processing module 110 when sensing is desired). In some cases, LCP 100 may control the generation of signals 504, 506, 508 and/or 510 by the accelerometer. For instance, LCP 100 may control when power is provided to the accelerometer, and the accelerometer may only generate signals 504, 506, 508 and/or 510 when power is provided to the accelerometer. In some cases, LCP 100 may switch the accelerometer from a lower-power state (e.g. a sleep mode) to a higher-power state (e.g. awake or active mode) during time periods where LCP 100 is to sense the accelerometer signal(s). During the lower-power state, the accelerometer may not provide an appreciable signal for LCP 100 to sense and/or sample. In some cases, and where processing module 110 is a digital device, an A/D converter may sample signals 504, 506, 508 and/or 510 when sensing is desired. These are just some examples of how signals 504, 506, 508 and/or 510 may be "sensed" during certain time periods.

LCP 100 may be configured to sense one or more signals during predetermined time periods. Such predetermined time periods may be represented by sensing periods 512*a*-512*d* in FIG. 5. Sensing periods 512*a*-512*d* may occur at regular intervals, such as every five seconds, every second, every eight hundred milliseconds, every seven hundred milliseconds, or any other suitable value. Alternatively, LCP 100 may initiate sensing periods 512*a*-512*d* after every beat, once every other beat, once every five beats, or at any other suitable frequency and/or duration. In at least some cases, LCP 100 may adjust the interval according to a heart rate of the patient such that successive sensing periods 512*a*-512*d* occur during the same portion of the cardiac cycle (e.g. when the heart is quiet such as between heart beats).

In some instances, LCP 100 may implement sensing periods 512*a*-512*d* based on one or more detected features of cardiac electrical signal 502. For instance, LCP 100 may detect one or more features of cardiac electrical signal 502, such as cardiac electrical events 511. Cardiac electrical events 511 may represent R-waves or other morphological features detected by LCP 100. Upon detection of cardiac electrical event 511, LCP 100 may initiate a time delay, such as time delay 514. Upon expiration of time delay 514, LCP 100 may initiate sensing periods 512*a*-512*d*, during which LCP 100 may "sense" one or more signals, such as signals 504, 506, 508 and/or 510. In at least some cases, LCP 100 may adjust time delay 514 based on the heart rate of the patient. For instance, when the heart rate is at a relatively higher heart rate, LCP 100 may shorten time delay 514, and when the heart rate is at a relatively lower heart rate, LCP 100 may lengthen time delay 514. This may help the LCP 100 consistently initiate sensing periods 512*a*-512*d* during the same or similar portion of the cardiac cycle (e.g. during the quit period between polarization/repolarizations of the heart).

In some instances, the length of time delay 514 may be chosen to align with a portion of the cardiac cycle where the heart is relatively mechanically inactive, such as shown in FIG. 5. For instance, time delay 514 may be chosen so that it expires between about fifty milliseconds to about one-hundred fifty milliseconds before the beginning of the next heartbeat. During this portion of the cardiac cycle, the heart muscle may be in a relatively relaxed state while filling with blood. Accordingly, during this portion of the cardiac cycle, the orientation of LCP 100 may be at a relatively consistent position. This may allow LCP 100 to more easily detect a current posture of the patient, as explained in more detail below. In other embodiments, an accelerometer or other sensor may be implanted in the patient outside of the heart, and may transmit an indication of posture to the LCP 100.

The signals depicted in FIG. 5 may represent signals acquired during normal cardiac function, e.g. when no tamponade condition is occurring. Notice that each of the accelerometer signals following each cardiac electrical event 511 are similar in shape and magnitude.

Figure 6:
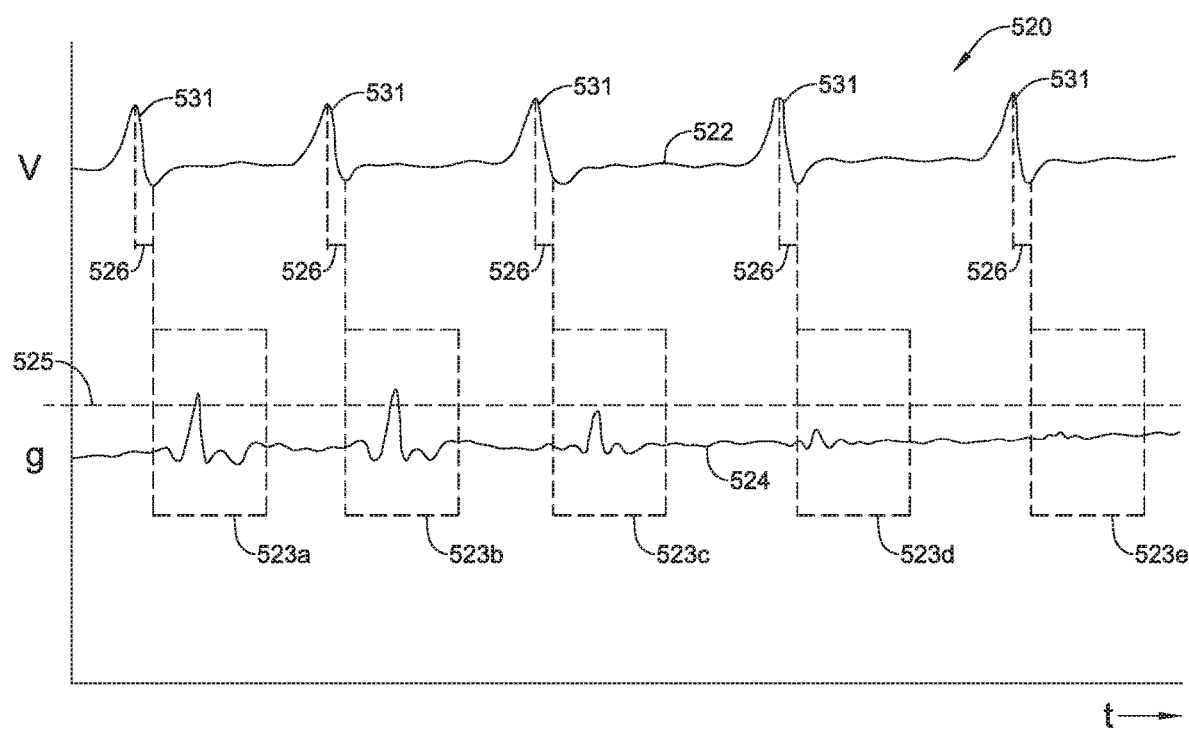
FIG. 6 is a graph showing an illustrative cardiac electrical signal and an illustrative accelerometer signal detected by an LCP.

FIG. 6 depicts graph 520 including an example cardiac electrical signal 522, including cardiac electrical events 531, and accelerometer signal 524 which represents a magnitude of the accelerometer of LCP 100, similar to signal 510 of FIG. 5. Graph 520 depicts signals 522 and 524 over multiple cardiac cycles where the patient is suffering from a tamponade condition. As can be seen in FIG. 6, the maximum amplitude of signal 524 diminishes over time throughout successive cardiac cycles. However, the maximum amplitude of the illustrative cardiac electrical signal 522 remains relatively constant over the same cardiac cycles. Accordingly, detecting a tamponade condition may be difficult using only the cardiac electrical signal.

Figure 7:
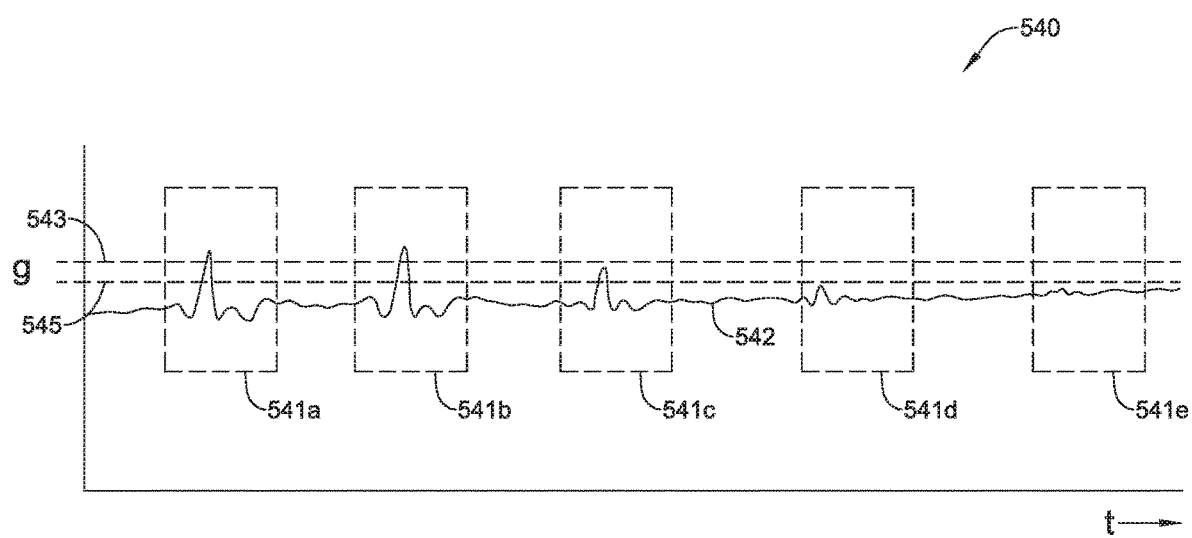
FIG. 7 is a graph showing an illustrative accelerometer signal detected by an LCP showing multiple thresholds, in accordance with techniques of the present disclosure.
Figure 8:
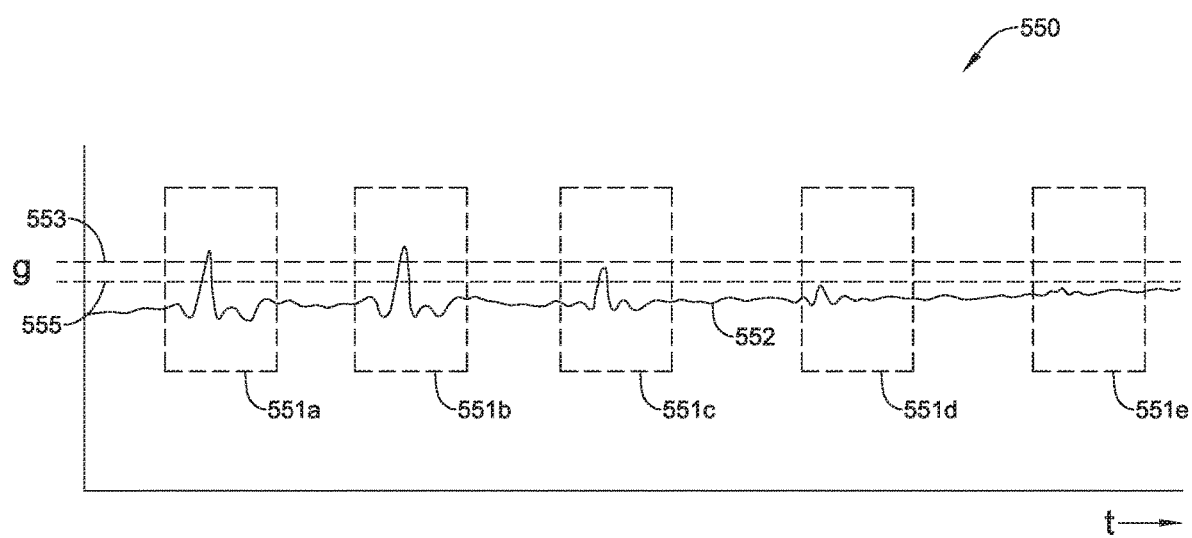
FIG. 8 is a graph showing an illustrative accelerometer signal detected by an LCP showing multiple thresholds, in accordance with techniques of the present disclosure.
Figure 9:
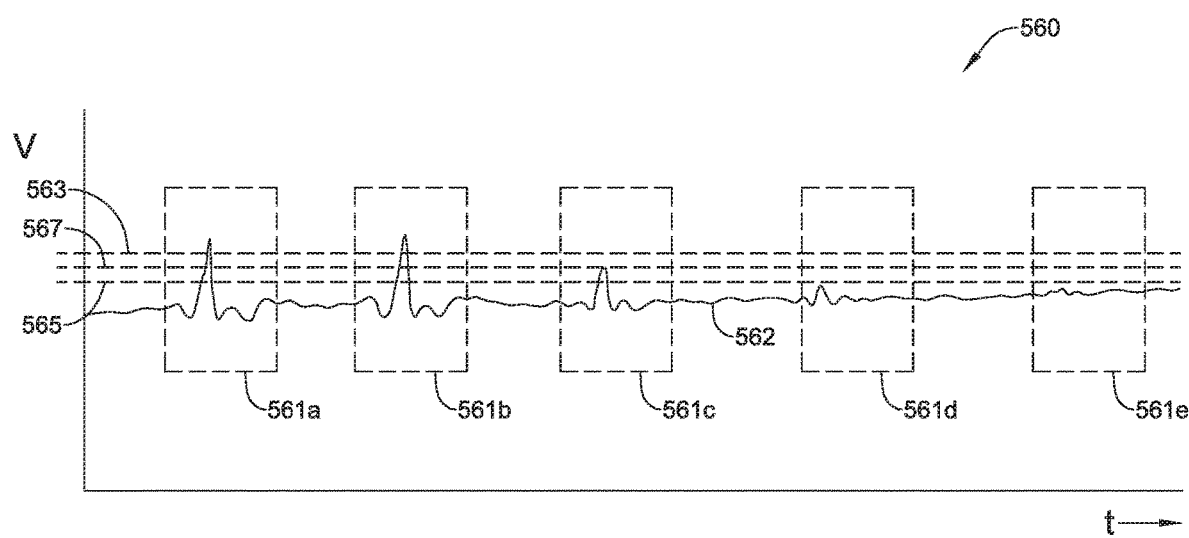
FIG. 9 is a graph showing an illustrative accelerometer signal detected by an LCP showing multiple thresholds, in accordance with techniques of the present disclosure.

While FIG. 6 shows the maximum amplitude of signal 524 diminish rapidly over only five (5) cardiac cycles, this has been intentionally compressed in time for ease of description only. In most cases, the maximum amplitude of signal 524 will diminish much more slowly, such as over minutes, hours or even days. FIGS. 7-9 have been similarly compressed in time for ease of description.

When LCP 100 is in the tamponade mode, LCP 100 may adjust how LCP 100 senses the accelerometer signal(s). As can be seen, time delay 526 of FIG. 6 is relatively shorter than time delay 514 of FIG. 5. The length of time delay 526 may be chosen to generally align with the contraction of the heart. This may help LCP 100 sense the accelerometer signals during sensing periods 523a-e that correspond to when the heart is actually contracting.

In some instances, time delay 526 may be about ten milliseconds, about fifteen milliseconds, about twenty milliseconds, about twenty-five milliseconds, about thirty milliseconds, about thirty-five milliseconds, or any other suitable period of time following a detected R-wave. In general, time delay 526 may have a value that is less than an electromechanical delay of the heart, which is the delay between when LCP 100 detects a cardiac electrical event 531 (e.g. R-wave) and an onset of cardiac wall motion or a threshold amount of cardiac wall motion. Sensing periods 523a-e may have a duration of about twenty-five milliseconds, about thirty milliseconds, about forty milliseconds, or about fifty milliseconds. However, in other embodiments, sensing periods 523a-e may be substantially longer, for instance, about half of a cardiac cycle of the patient, about three quarters of the cardiac cycle of the patient, or may span an entire cardiac cycle of the patient. In some additional or alternative embodiments, time delay 526 and/or sensing periods 523a-e may have lengths that change along with the heart rate of the patient. As one example, for relatively higher heart rates, time delay 526 and/or sensing periods 523a-e may be shorter than for relatively lower heart rates.

In general, LCP 100 may be able to use accelerometer signals sensed during a portion of the cardiac cycle that corresponds to sensing periods 523a-e to determine whether a tamponade condition is occurring. As mentioned previously, when tamponade is occurring, blood or other fluid may be pooling in the pericardial sac, preventing full relaxation of the heart between contractions. The pooled blood may then prevent the heart from contracting to as great of an extent as under normal conditions. This difference in the motion of the heart may be seen through the sensed accelerometer signals.

To determine whether a tamponade condition is occurring, in some instances, LCP 100 may compare a maximum amplitude of signal 524 within a sensing window to a threshold, such as threshold 525. If LCP 100 determines that the maximum amplitude of signal 524 is less than threshold 525, LCP 100 may determine that a tamponade condition is occurring. In other embodiments, after determining that the maximum amplitude of signal 524 is less than threshold 525 in a first sensing window, such as sensing window 523c, LCP 100 may continue to monitor signal 524 during subsequent sensing windows, for example sensing windows 523d and 523e, and comparing signal 524 to threshold 525 during those subsequent sensing windows. In these embodiments, LCP 100 may only determine that a tamponade condition is occurring if the maximum amplitude of signal 524 in a second, subsequent sensing window is also less than threshold 525. In still further embodiments, LCP 100 may require the maximum amplitude of signal 524 to be less than threshold 525 in three (or more) consecutive sensing windows before determining that a tamponade condition is occurring.

In still other embodiments, LCP 100 may require the maximum amplitude of signal 524 to be less than threshold 525 in four, five, ten, or twenty consecutive sensing windows, or any other suitable number of sensing windows, before determining that a tamponade condition is occurring. Other options further include LCP 100 requiring that the maximum amplitude of signal 524 to be less than threshold 525 in three out of five consecutive sensing windows, five out of ten consecutive sensing windows, or any other suitable combinations before determining that a tamponade condition is occurring.

In even more additional or alternative embodiments, after LCP 100 determines the maximum amplitude of signal 524 is less than threshold 525, LCP 100 may track a period of time. LCP 100 may then determine that a tamponade condition is occurring if the maximum amplitude of signal 524 does not cross back above threshold 525 within the predefined period of time. In some instances, LCP 100 may switch to continuously or substantially continuously sensing signal 524 (e.g. turn on and/or sample accelerometer signal continuously or substantially continuously). In other embodiments, however, LCP 100 may maintain sensing signal 524 only in sensing windows. Accordingly, rather than counting a number of sensing windows, LCP 100 may simply monitor signal 524 within any number of subsequent sensing windows which fall within the tracked period of time In other alternative embodiments, LCP 100 may track a moving average of the maximum amplitude of signal 524 over about three, about five, about ten, about fifteen, or about twenty cardiac cycles, or any other suitable number of cardiac cycles, and may store the determined moving averages in a memory. During a tamponade condition, this moving average will steadily decrease over time as the heart loses its ability to expand and pump blood due to blood pooling in the pericardial sac. Accordingly, in some embodiments, LCP 100 may compare the moving average to a threshold to determine whether a tamponade condition is occurring. In other or additional embodiments, LCP 100 may determine whether the stored moving averages decrease in a monotonic fashion. If LCP 100 determines that about five, about ten, about fifteen, or any other suitable number of consecutive determined moving averages decrease in a monotonic fashion, LCP 100 may determine that a tamponade condition is occurring.

Alternatively, LCP 100 may determine the slopes between consecutive determined moving averages. If LCP 100 determines that a threshold number, such as three, five, ten, fifteen, or twenty, of consecutive slopes are negative, LCP 100 may determine that a tamponade condition is occurring. Also, the magnitude of the slope(s) may be taken into consideration. A larger slope may indicate a more severe tamponade condition, and thus the LCP 100 may determine that a tamponade condition is occurring sooner.

Although the above tamponade detection techniques included monitoring for tamponade over a relatively short time period, e.g. a number of cardiac cycles, in some additional or alternative embodiments, LCP 100 may be configured to monitor for a tamponade condition over longer periods of time. For instance, LCP 100 may be configured to monitor for tamponade once an hour, once every few hours, twice a day, or once a day. In these embodiments, LCP 100 may monitor, for example, the maximum amplitude of signal 524 during one or more sensing periods during each chosen time interval. LCP 100 may then compare the sensed maximum amplitude of signal 524 during each of these chosen time intervals to determine if there is a trend. For example, LCP 100 may compare these determined differences to one or more thresholds, as above, to determine if a tamponade condition is occurring. This may facilitate detection of slow-onset tamponade conditions.

FIG. 7 depicts another embodiment where LCP 100 may be configured to determine that a tamponade condition is occurring. FIG. 7 depicts a graph 540 showing an accelerometer signal 542, which may represent a magnitude of acceleration from an accelerometer of LCP 100. In the example of FIG. 7, LCP 100 may employ multiple thresholds in determining whether a tamponade condition is occurring. For example, LCP 100 may initially monitor accelerometer signal 542 during sensing windows 541a-541e to determine when a maximum amplitude of signal 542 within a sensing window falls below first threshold 543. Once LCP 100 determines that signal 542 has fallen below first threshold 543, LCP 100 may monitor accelerometer signal 542 to determine if, or when, accelerometer signal 542 falls below second threshold 545. In the example of FIG. 7, LCP 100 would determine that accelerometer signal 542 falls below second threshold 545 in the next sensing window 541d. At this point, after accelerometer signal 542 has fallen below the first threshold 543 and then subsequently fallen below the second threshold 545, LCP 100 may determine that a tamponade condition is occurring, as this trend may indicate declining mechanical motion of the heart. Of course, in additional embodiments, LCP 100 may only determine that a tamponade condition is occurring after determining that a maximum amplitude of accelerometer signal 542 in multiple subsequent sensing windows is still below second threshold 545, for instance in any manner that was described with respect to FIG. 6.

Of course, in some cases, the maximum amplitude of accelerometer signal 542 may be above both first threshold 543 and second threshold 545 in a first sensing window and may be less than both first threshold 543 and second threshold 545 in a next sensing window. In such embodiments, LCP 100 may monitor subsequent sensing windows and determine whether the maximum amplitude of accelerometer signal 542 stays below second threshold 545. If LCP 100 determines the maximum amplitude of accelerometer signal 542 stays below second threshold 545 for one or more subsequent sensing windows, LCP 100 may then determine that a tamponade condition is occurring. In such embodiments, the tamponade condition may worsen too quickly for LCP 100 to sense the decline in mechanical motion of the heart, and LCP 100 may instead rely simply on a consistent indication of low cardiac motion to determine that a tamponade condition is occurring.

In some embodiments, first threshold 543 may be set as a certain percentage of a maximum value of sensed signal 542 in a sensing window when signal 542 is sensed under conditions where it is known that tamponade is not occurring. For instance, first threshold 543 may be set at about seventy-five percent of the maximum value of sensed signal 542 in a sensing window. However, in other embodiments, first threshold 543 may be set at different percentages of the maximum value of sensed signal 542 in a sensing window, such as about fifty percent, about sixty-percent, about seventy percent, about eighty percent, about eighty-five percent, about ninety percent, or any other suitable value. In some embodiments, the value of second threshold 543 may be programmable.

Second threshold 545 may be set at a certain percentage of first threshold 543. For instance, second threshold 545 may be set at about seventy-five percent of first threshold 543. However, in other embodiments, second threshold 545 may be set at different percentages of first threshold 543, such as about fifty percent, about sixty-percent, about seventy percent, about eighty percent, about eighty-five percent, about ninety percent, or any other suitable value. In some embodiments, the value of second threshold 545 may be programmable.

FIG. 8 depicts still another embodiment where LCP 100 may be configured to determine that a tamponade condition is occurring. FIG. 8 depicts a graph 550 showing an accelerometer signal 552, which may represent a magnitude of acceleration from an accelerometer of LCP 100. In the example of FIG. 8, LCP 100 may employ multiple thresholds in determining whether a tamponade condition is occurring. For example, LCP 100 may initially monitor accelerometer signal 552 during sensing windows 551a-551e to determine when a maximum amplitude of accelerometer signal 552 within a sensing window falls below first threshold 553.

Once LCP 100 determines that the maximum amplitude of signal 552 has fallen below first threshold 553, such as in sensing window 551c, LCP 100 may monitor accelerometer signal 552 to determine if, or when, accelerometer signal 552 rises above second threshold 555. For example, LCP 100 may monitor accelerometer signal 552 for a number of subsequent sensing windows, or for a predefined period of time, after detecting that the maximum amplitude of accelerometer signal 552 is less than first threshold 553. If LCP 100 determines that the maximum amplitude of accelerometer signal 552 did not rise above second threshold 555 within the predetermined number of subsequent sensing windows, or within the predefined period of time, LCP 100 may determine that a tamponade condition is occurring. If LCP 100 determines that accelerometer signal 552 did rise above second threshold 555 within the predetermined number of subsequent sensing windows, or within the predefined period of time, LCP 100 may then switch back to monitoring whether the maximum amplitude of accelerometer signal 552 is below first threshold 553.

In some embodiments, first threshold 553 may be set as a certain percentage of a maximum value of sensed signal 552 in a sensing window when signal 552 is sensed under conditions where it is known that tamponade is not occurring. For instance, first threshold 553 may be set at about seventy-five percent of the maximum value of sensed signal 552 in a sensing window. However, in other embodiments, first threshold 553 may be set at different percentages of the maximum value of sensed signal 552 in a sensing window, such as about fifty percent, about sixty-percent, about seventy percent, about eighty percent, about eighty-five percent, about ninety percent, or any other suitable value. In some embodiments, the value of second threshold 553 may be programmable.

Second threshold 555 may be may be set at a certain percentage of first threshold 543. For instance, second threshold 545 may be set at about seventy-five percent of first threshold 543. However, in other embodiments, second threshold 545 may be set at different percentages of first threshold 543, such as about fifty percent, about sixty-percent, about seventy percent, about eighty percent, about eighty-five percent, about ninety percent, or any other suitable value. In some embodiments, the value of second threshold 555 may be programmable.

FIG. 9 depicts still another embodiment where LCP 100 may be configured to determine that a tamponade condition is occurring. FIG. 9 depicts a graph 560 showing an accelerometer signal 562, which may represent a magnitude of acceleration from an accelerometer of LCP 100. In the example of FIG. 9, LCP 100 may employ multiple thresholds in determining whether a tamponade condition is occurring. For example, LCP 100 may initially monitor accelerometer signal 562 during sensing windows 561a-561e to determine when a maximum amplitude of accelerometer signal 562 within a sensing window falls below first threshold 563.

Once LCP 100 determines that the maximum amplitude of accelerometer signal 562 has fallen below first threshold 563, such as in sensing window 561c, LCP 100 may monitor accelerometer signal 562 to determine whether accelerometer signal 562 falls below second threshold 565 or rises above third threshold 567. For example, LCP 100 may monitor accelerometer signal 562 for a number of subsequent sensing windows, or for a predefined period of time, after detecting that the maximum amplitude of accelerometer signal 562 is less than first threshold 563. If LCP 100 determines that the maximum amplitude of accelerometer signal 562 rises above third threshold 567 before falling below second threshold 565, LCP 100 may go back to determining whether the maximum amplitude of accelerometer signal 562 is below first threshold 563. However, if LCP 100 determine that the maximum amplitude of accelerometer signal 562 does not rise above third threshold 567 within the predetermined number of subsequent sensing windows, or for the predefined period of time, LCP 100 may determine that a tamponade condition is occurring. Additionally, if LCP 100 determines that the maximum amplitude of accelerometer signal 562 falls below second threshold 565 at any point, LCP 100 may determine a tamponade condition is occurring, even if the predetermined number of subsequent sensing windows have not occurred, or the predefined period of time ran out.

In some embodiments, first threshold 563 may be set as a certain percentage of a maximum value of sensed signal 562 in a sensing window when signal 562 is sensed under conditions where it is known that tamponade is not occurring. For instance, first threshold 563 may be set at about seventy-five percent of the maximum value of sensed signal 562 in a sensing window. However, in other embodiments, first threshold 563 may be set at different percentages of the maximum value of sensed signal 562 in a sensing window, such as about fifty percent, about sixty-percent, about seventy percent, about eighty percent, about eighty-five percent, about ninety percent, or any other suitable value. In some embodiments, the value of second threshold 563 may be programmable.

Second threshold 565 and/or third threshold 567 may be set at a certain percentage of first threshold 563. For instance, third threshold 567 may be set at about seventy-five percent of first threshold 563. However, in other embodiments, third threshold 567 may be set at different percentages of first threshold 563, such as about fifty percent, about sixty-percent, about seventy percent, about eighty percent, about eighty-five percent, about ninety percent, or any other suitable value. In some embodiments, second threshold 565 may be set at about fifty percent of first threshold 563. However, in other embodiments, second threshold 565 may be set at different percentages of first threshold 563, such as about twenty-five percent, about thirty percent, about thirty-five percent, about forty percent, about forty-five percent, or any other suitable value. In some embodiments, the value of second and/or third threshold 565, 567 may be programmable.

Although the embodiments of FIGS. 6-9 all use the magnitude of the accelerometer signal, it should be understood that this is for illustrative purposes only. In other embodiments, LCP 100 may use other signals to determine whether a tamponade condition is occurring. For example, LCP 100 may use any signal received from the accelerometer, such as the different signals representing different axes of the accelerometer, to determine whether a tamponade condition is occurring. LCP 100 may further process the accelerometer signal to derive one or more other signals for use in determining whether a tamponade condition is occurring. As one example, LCP 100 may double integrate the accelerometer signal to determine a displacement signal, representing the displacement of the accelerometer over time, which correlates to displacement of the heart wall. LCP 100 may compare a maximum amplitude of a portion of this displacement signal, such as during a filling of the heart, to one or more thresholds to determine whether a tamponade condition is occurring. For instance, the maximum amplitude of the displacement signal in the monitored portion may relate to the amount of movement of the cardiac wall during filling. As blood pools in the pericardial sac, the maximum value of this signal will decrease over time. Accordingly, LCP 100 may monitor whether this value decreases below one or more threshold and, if so, determine an occurrence of a tamponade condition. Like with the accelerometer signal, LCP 100 may use a feature of the cardiac electrical signal to determine which portion of the displacement signal to monitor. For instance, LCP 100 may track a period of time from a cardiac electrical event and begin monitoring the displacement signal for the maximum amplitude within a sensing window beginning upon expiration of the period of time. In at least some embodiments, the period of time used for the accelerometer signal and the period of time used for the displacement signal are different.

In still other embodiments, LCP 100 may include other sensors and may use signals from those sensors to determine whether a tamponade condition is occurring. Some other example sensors include a pressure sensor and/or a gyroscope. When provided, a gyroscope may be a multi-axis gyroscope and generate signals similar to the multi-axis accelerometer described above. In some cases, as mentioned previously, signals generated by a gyroscope may have a certain synchrony with the cardiac electrical signals which may change during a tamponade condition. Loss of the synchrony of a peak value of the gyroscope signal and the cardiac electrical events may indicate a tamponade condition is occurring. In other embodiments, LCP 100 may employ any of the techniques described with respect to the accelerometer signal to the gyroscope signal to determine whether a tamponade condition is occurring.

Further, as a tamponade condition is worsening, the intra-chamber blood pressure, and in particular the intra-chamber blood pressure as the heart contracts to pump the blood, may change over time in a diminishing manner. In these embodiments, LCP 100 may monitor an intra-chamber blood pressure signal detected via a pressure sensor and/or detected via heart sounds via an accelerometer or the like. For example, the amplitude of the first heart sound (S1), which can be detected by an accelerometer or the like, is proportional to the rate of left ventricular pressure rise (LV dP/dt). LCP 100 may compare a maximum amplitudes of this blood pressure signal taken over time to one or more thresholds. In general, any of the threshold techniques described above with respect to the maximum amplitude of the accelerometer may be applied to the blood pressure signal.

In some further embodiments, LCP 100 may monitor a time duration of the peak of the dP/dt signal, such as by monitoring how long the dP/dt signal stays within a certain percentage of the peak dP/dt signal value over a cardiac cycle, such as within about three percent, about five percent, about eight percent, or about ten percent. During a tamponade condition, this time value may lengthen. Accordingly, LCP 100 may compare this determined time value to a threshold, and LCP 100 may determine that a tamponade condition is occurring if the value rises above a threshold.

In still other embodiments, LCP 100 may monitor heart sounds for indications of valve closures, for instance based on deflections in the heart sounds signal. If LCP 100 determines that there is a lack of detected expected valve closures, LCP 100 may determine an occurrence of a tamponade condition. For instance, LCP 100 may expect to detect two, three, or four heart sound features in the heart sounds signal for each cardiac cycle. If LCP 100 detects less than is expected, LCP 100 may determine that a tamponade condition is occurring. Additionally, or alternatively, LCP 100 may determine that a tamponade condition is occurring if a monitored maximum amplitude of the heart sounds signal falls below a threshold for one or more cardiac cycles, or the heart sounds signal differs from a template heart sounds signal.

Accordingly, in any these above embodiments, instead of using signals from an accelerometer, LCP 100 may use signals from the gyroscope, the blood pressure sensors, or any other sensors in any manner described above to determine whether a tamponade condition is occurring.

In still other embodiments, LCP 100 may use multiple signals to determine whether tamponade is occurring. For instance, LCP 100 may perform analyses on multiple signals generated by the accelerometer, gyroscope, and/or blood pressure sensor. In some of these embodiments, LCP 100 may determine that a tamponade condition is occurring if analysis on any one signal indicates a tamponade condition. However, in other embodiments, LCP 100 may only determine that a tamponade condition is occurring if multiple of the signals indicate a tamponade condition, such as two signals, three signals, four signals, all of the signals, or any other suitable number of signals.

Where LCP 100 uses multiple signals to determine whether tamponade is occurring, LCP 100 may, in some examples, analyze the signals in a cascading fashion. For instance, LCP 100 may initially only monitor a single signal. After determining that the first signal indicates that a tamponade condition is occurring, LCP 100 may then begin to monitor a second signal. In some instances, only after the second signal has indicated that a tamponade condition is occurring does the LCP 100 determine that a tamponade condition is occurring. In some cases, LCP 100 may be able to cascade the analysis of the signals in order to save energy. For instance, in some embodiments LCP 100 may be configured to monitor a first signal from an accelerometer while the other channels of the accelerometer or other sensors are turned off. Only after the first accelerometer signal indicates that a tamponade condition is occurring does the LCP 100 turn on another channel of the accelerometer or other sensor(s) in order to analyze a second signal. In different embodiments, LCP 100 may use any of the above described signal(s) in any cascading combination in order to determine whether a tamponade condition is occurring.

Additionally, although the techniques of the present disclosure were described in relation to a maximum amplitude of the signal from the accelerometer or other sensor, in other embodiments, LCP 100 may use different characteristics of the signals. As one example, the value of the integral, or double integral, of the analyzed signal within the sensed window may be used instead of the maximum amplitude of the signal. In these embodiments, the value of the integral or double integral may be compared to one or more thresholds, in a similar manner to that described with respect to the maximum amplitude of the signal, to determine whether a tamponade condition is occurring. In another example, a peak width of a signal may be used. For example, as detailed, above, how long a dP/dt signal stays within a certain percentage of the peak dP/dt signal value may be used to determine if a tamponade condition is occurring.

After determining that a tamponade condition is occurring, LCP 100 may generate an alarm signal or message and communicate the alarm signal to a device external to LCP 100. For instance, where LCP 100 is part of a medical device system, such as system 400, LCP 100 may communicate the alarm signal to external support device 420. External support device 420 may then generate a visual or audible alarm to notify a user in the vicinity of external support device 420 that LCP 100 has determined that a tamponade condition is occurring. In other embodiments, LCP 100 may communicate the alarm signal to another internally implanted device, for instance pulse generator 406, and the other internally implanted device may communicate the alarm signal to a device outside of the patient. In some embodiments, LCP 100, or another device which receives the alarm signal from LCP 100, may be connected to one or more wireless networks. LCP 100, or another device of the system, may connect to the wireless network to communicate the alarm signal to a remote device, such as a pager, cell phone, or other remote device connected to the wireless network.

Additionally, although the above described techniques are centered around LCP 100 performing the sensing and determining functions, where LCP 100 is part of a device system, such as system 400 of FIG. 4, other devices of the system may perform at least some of these functions. For example, LCP 100 may monitor or sense signals from an accelerometer or pressure sensor of the LCP 100 and communicate those signals, or portions of those signals, to another device, such as pulse generator 406. Pulse generator 406 may then determine whether a tamponade condition is occurring. If pulse generator 406 determines that a tamponade condition is occurring, pulse generator 406 may then communicate an indication that a tamponade condition is occurring, for instance as described with respect to LCP 100. In other embodiments, the device doing the determining, based on signals received from LCP 100, may be external support device 406.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. A method for detecting a tamponade condition of a patient's heart after attachment of a leadless cardiac pacemaker to the patient's heart, the leadless cardiac pacemaker having a motion sensor that produces a motion signal, the method comprising:
    monitoring two or more electrodes of the leadless cardiac pacemaker to detect a cardiac electrical signal of the patient's heart;
    monitoring the motion signal of the leadless cardiac pacemaker;
    identifying a characteristic of the motion signal;
    determining when the tamponade condition is indicated based at least in part on whether the identified characteristic of the motion signal changes over time in a predetermined way during a sensing window that is defined at least in part by one or more characteristics of the cardiac electrical signal; and
    in response to determining that the tamponade condition is indicated, providing a notification of the tamponade condition for use by a physician to take corrective action.

2. The method of claim 1, wherein the motion sensor comprises an accelerometer, and the motion signal comprises an accelerometer signal.

3. The method of claim 2, wherein the accelerometer comprises a multi-axis accelerometer, and the accelerometer signal is a multi-axis accelerometer signal.

4. The method of claim 2, wherein the identified characteristic of the motion signal is indicative of a displacement of a wall of the patient's heart.

5. The method of claim 2, wherein the identified characteristic of the motion signal is indicative of a filling volume of the patient's heart.

6. The method of claim 2, wherein the identified characteristic of the motion signal is indicative of a heart sound of the patient's heart.

7. The method of claim 2, wherein the leadless cardiac pacemaker further comprises a pressure sensor that produces a pressure signal, the method further comprising:
    determining when the tamponade condition is indicated based at least in part on whether the identified characteristic of the motion signal changes over time in a predetermined way and based on the pressure signal.

8. The method of claim 1, wherein the motion sensor comprises a gyroscope and the motion signal comprises a gyroscope signal.

9. The method of claim 8, wherein the gyroscope comprises a multi-axis gyroscope, and the gyroscope signal is a multi-axis gyroscope signal.

10. The method of claim 8, further comprising:
    monitoring two or more electrodes of the leadless cardiac pacemaker to detect a cardiac electrical signal of the patient's heart; and
    determining when the tamponade condition is indicated based at least in part on whether a synchrony between the identified characteristic of the gyroscope signal changes over time relative to the cardiac electrical signal.

11. The method of claim 1, wherein the leadless cardiac pacemaker performs the monitoring, determining and providing steps.

12. The method of claim 1, wherein the leadless cardiac pacemaker performs the monitoring step.

13. The method of claim 1, wherein an external device programmer performs one or more of the monitoring, determining and providing steps.

14. The method of claim 1, wherein providing the notification comprises communicating a message from the leadless cardiac pacemaker for reception by an external device programmer.

15. A leadless cardiac pacemaker for use in pacing a patient's heart, comprising:
    a plurality of electrodes;
    a motion sensor for providing an motion signal;
    a controller operatively coupled to the plurality of electrodes and the motion sensor, the controller configured to:
        monitor two or more of the plurality of electrodes to detect a cardiac electrical signal of the patient's heart;
        monitor the motion signal of the motion sensor over time;
        identifying a characteristic of the motion signal;
        determining when a tamponade condition is indicated based at least in part on whether the identified characteristic of the motion signal changes over time in a predetermined way during a sensing window that is defined at least in part by one or more characteristics of the cardiac electrical signal; and
        in response to determining that the tamponade condition is indicated, communicate a notification of the tamponade condition for use by a physician to take corrective action.

16. The leadless cardiac pacemaker of claim 11, wherein the motion sensor comprises an accelerometer and/or a gyroscope.

17. A leadless cardiac pacemaker, comprising:
    a plurality of electrodes;
    a motion sensor for providing a motion signal;
    a controller operatively coupled to the plurality of electrodes and the motion sensor, the controller configured to:
        monitor two or more of the plurality of electrodes to detect a cardiac electrical signal of the patient's heart;
        monitor an indication of physical motion of a patient's heart over time using the motion sensor;
        determine when the indication of the physical motion of the patient's heart changes over time in a predetermined way during a sensing window that is defined at least in part by one or more characteristics of the cardiac electrical signal; and
        when it is determined that the indication of the physical motion of the patient's heart has changed over time in the predetermined way, communicate a notification of a possible tamponade condition for reception by a remote device that is remote from the leadless cardiac pacemaker.

18. The leadless cardiac pacemaker of claim 17, wherein the controller is further configured to monitor a heart rate of the patient's heart over time and to determine if the heart rate increases over time by at least a predetermined heart rate amount.

19. The leadless cardiac pacemaker of claim 18, wherein the controller communicates a notification of the possible tamponade condition when it is determined that the indication of the physical motion of the patient's heart has changed over time in the predetermined way and the heart rate of the patient's heart has increased over time by at least the predetermined heart rate amount.

* * * * *